(12) United States Patent
Ma et al.

(10) Patent No.: US 11,918,194 B2
(45) Date of Patent: Mar. 5, 2024

(54) OSTEOTOMY CALIBRATION METHOD, CALIBRATION DEVICE AND ORTHOPEDIC SURGERY SYSTEM

(71) Applicant: Suzhou MicroPort Orthobot Co., Ltd., Jiangsu (CN)

(72) Inventors: Jingyang Ma, Jiangsu (CN); Feng Sun, Jiangsu (CN); Hui Shao, Jiangsu (CN); Chao He, Jiangsu (CN); Pengfei Liu, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 962 days.

(21) Appl. No.: 16/856,489

(22) Filed: Apr. 23, 2020

(65) Prior Publication Data
US 2021/0153851 A1 May 27, 2021

(30) Foreign Application Priority Data
Nov. 21, 2019 (CN) .......................... 201911151227.5

(51) Int. Cl.
*A61B 17/00* (2006.01)
*A61B 17/14* (2006.01)
(Continued)

(52) U.S. Cl.
CPC .............. *A61B 17/00* (2013.01); *A61B 34/30* (2016.02); *A61B 2017/00199* (2013.01);
(Continued)

(58) Field of Classification Search
CPC ......... A61B 17/17; A61B 34/30; A61B 90/50; A61B 2034/2072; A61B 2017/00477;
(Continued)

(56) References Cited

U.S. PATENT DOCUMENTS

2014/0039520 A1  2/2014  Haider et al.
2014/0206990 A1*  7/2014  Epstein .................. A61B 90/37
                                                        600/587
(Continued)

FOREIGN PATENT DOCUMENTS

CN         101862220 A    10/2010
CN         107468350 A    12/2017
(Continued)

*Primary Examiner* — Kevin T Truong
*Assistant Examiner* — Diana Jones
(74) *Attorney, Agent, or Firm* — MUNCY, GEISSLER, OLDS & LOWE, P.C.

(57) ABSTRACT

An osteotomy calibration method, calibration device, and an orthopedic surgery system are provided by present application. Firstly using the osteotomy calibration device to obtain the calculated position information of the current osteotomy plane, and then determining a position error between the calculated position information and a predetermined position information of a planned osteotomy plane, and if the position error exceeds a preset value, calculating and transmitting a relocation information to a robotic arm to control and relocate the robotic arm. By comparing and identifying the position error between the current osteotomy plane formed by the first osteotomy and the planned predetermined osteotomy plane, relocating the robotic arm, and performing a secondary correction of the osteotomy plane. In addition, by relocating the robotic arm and secondary correction of the osteotomy plane, additional bone nails which is to fix the navigation tool to the bone can be avoided.

11 Claims, 3 Drawing Sheets

(51) Int. Cl.
   *A61B 17/15*   (2006.01)
   *A61B 17/16*   (2006.01)
   *A61B 34/00*   (2016.01)
   *A61B 34/10*   (2016.01)
   *A61B 34/20*   (2016.01)
   *A61B 34/30*   (2016.01)

(52) U.S. Cl.
   CPC ..... *A61B 2017/00725* (2013.01); *A61B 17/14* (2013.01); *A61B 17/151* (2013.01); *A61B 17/1675* (2013.01); *A61B 2034/107* (2016.02); *A61B 2034/2051* (2016.02); *A61B 2034/2055* (2016.02); *A61B 2034/2068* (2016.02); *A61B 2034/2072* (2016.02); *A61B 2034/743* (2016.02)

(58) Field of Classification Search
   CPC ...... A61B 2034/107; A61B 2034/2051; A61B 2034/2055; A61B 2034/743; A61B 17/14; A61B 17/151; A61B 17/1675; A61B 2017/00199
   See application file for complete search history.

(56) References Cited

U.S. PATENT DOCUMENTS

2018/0193097 A1* 7/2018 McLachlin ............ A61B 34/20
2019/0053852 A1* 2/2019 Schoenefeld .......... A61B 90/37

FOREIGN PATENT DOCUMENTS

| | | |
|---|---|---|
| CN | 107920860 A | 4/2018 |
| CN | 109199586 A | 1/2019 |
| EP | 1113760 B1 | 11/2008 |
| EP | 3569159 A1 | 11/2019 |
| JP | 2017535406 A | 11/2017 |
| JP | 2019122768 A | 7/2019 |
| WO | WO-2017/204832 A1 | 11/2017 |
| WO | WO-2018/189725 A1 | 10/2018 |
| WO | WO-2018/213835 A1 | 11/2018 |

* cited by examiner

OSTEOTOMY CALIBRATION METHOD, CALIBRATION DEVICE AND ORTHOPEDIC SURGERY SYSTEM

CROSS-REFERENCE TO RELATED APPLICATION

This application claims the priority of Chinese patent application number 201911151227.5, filed on Nov. 21, 2019, the entire contents of which are incorporated herein by reference.

TECHNICAL FIELD

The present application relates to the field of robot-assisted surgery system and method, and in particular, to an osteotomy calibration method, calibration device, a readable storage medium, and an orthopedic surgery system.

BACKGROUND

In an artificial joint replacement surgery, a variety of positioners, navigation devices and the like are needed for osteotomy before installation of the artificial joint so that the accuracy of the osteotomy operation could be ensured. Different methods have been proposed to help surgeons achieve the positioning of osteotomy navigation tools during total knee arthroplasty (TKA) surgery. Generally, in the existing robot-assisted surgery system, an osteotomy tool is arranged at the end of the robotic arm, and the movement of the osteotomy tool is controlled by the robotic arm to realize the positioning of the osteotomy tool during knee arthroplasty surgery. However, the accuracy is determined by the absolute positioning accuracy of the robotic arm, and the osteotomy surface cannot be tracked and calibrated during osteotomy, which affects the accuracy of the operation. In addition, during osteotomy, the saw blade swings in a direction perpendicular to the saw blade due to the force working on the saw blade, which may easily cause an error between the planned osteotomy position and the actual osteotomy position.

SUMMARY OF THE INVENTION

An object of the present application is to provide an osteotomy calibration method, calibration device, a readable storage medium, and an orthopedic surgery system so as to solve the problem of low accuracy of the existing osteotomy.

To solve the above technical problems, according to a first aspect of the present application, there is provided an osteotomy calibration method, including:

obtaining a calculated position information of a current osteotomy plane using an osteotomy calibration device;

determining a position error between the calculated position information and a predetermined position information based on a planned osteotomy plane, and if the position error exceeds a preset value, calculating and transmitting a relocation information to a robotic arm so as to control and relocate the robotic arm.

Optionally, in the osteotomy calibration method, the osteotomy calibration device includes a position tracking calibration tool, and wherein the step of obtaining the calculated position information of the current osteotomy plane using the osteotomy calibration device includes:

obtaining a point cloud information according to a movement of the position tracking calibration tool on the current osteotomy plane, or according to a scan for the current osteotomy plane by the position tracking calibration tool;

collecting the point cloud information obtained by the position tracking calibration tool, and fitting the point cloud information to a fitting plane; and calculating a position information of the fitting plane, and defining the position information of the fitting plane as the calculated position information of the current osteotomy plane.

Optionally, in the osteotomy calibration method, the position tracking calibration tool is used to calibrate two or more current osteotomy planes, and wherein, prior to fitting the point cloud information to the fitting plan, the step of obtaining the calculated position of the current osteotomy plane using the osteotomy calibration device further includes:

dividing the point cloud information into respective groups corresponding to the two or more current osteotomy planes through clustering; and for each group of the groups of point cloud information, removing invalid point cloud information from the group, and fitting remaining point cloud information in the each group to a corresponding fitting plane.

Optionally, in the osteotomy calibration method, the step of determining the position error between the calculated position information and the predetermined position information includes, for each of the two or more current osteotomy planes:

matching the calculated position information of the current osteotomy plane with the predetermined position information of the corresponding planned osteotomy plane by clustering; and calculating the position error between the calculated position information of the current osteotomy plane and the predetermined position information of the corresponding planned osteotomy plane.

Optionally, in the osteotomy calibration method, the movement of the position tracking calibration tool on the current osteotomy plane includes an S-shaped, Z-shaped sliding, a multi-point click movement or any combination thereof.

Optionally, in the osteotomy calibration method, the osteotomy calibration device includes a displacement calibration tool for calibrating two or more current osteotomy planes, and wherein the step of obtaining the calculated position information of the current osteotomy plane using the osteotomy calibration device includes, for each of the two or more current osteotomy planes:

acquiring a position information of a corresponding sensing surface of the displacement calibration tool by abutting at least a part of the sensing surface on the current osteotomy plane, the sensing surface provided with a trackable element;

acquiring a displacement information of the current osteotomy plane with respect to the sensing surface;

calculating the calculated position information of the current osteotomy plane based on the displacement information of the current osteotomy plane with respect to the sensing surface and a position information of the sensing surface provided with the trackable element.

Optionally, in the osteotomy calibration method, the step of determining the position error between the calculated position information and the predetermined position information includes:

matching the calculated position information of each of the two or more current osteotomy planes with the predetermined position information of a corresponding planned osteotomy plane by clustering; and calculating the position error between the calculated position information of each of the two or more current osteotomy planes and the predetermined position information of the corresponding planned osteotomy plane.

To solve the above technical problems, according to a second aspect of the invention, there is provided an osteotomy calibration device, comprising: an acquisition unit and a position tracking unit; wherein:

the acquisition unit is configured to acquire a position information of a current osteotomy plane;

the position tracking unit is connected to the acquisition unit, and the position tracking unit is configured for position tracking by a navigation device;

the position information of the current osteotomy plane acquired by the acquisition unit and a position information of the position tracking unit in the navigation device is used to determine a calculated position information of the current osteotomy plane.

Optionally, in the osteotomy calibration device, the osteotomy calibration device comprising: a position tracking calibration tool including a detection part and a trackable element connected to the detection part, the detection part is configured as the acquisition unit, and the trackable element is configured as the position tracking unit.

Optionally, in the osteotomy calibration device, the position tracking calibration tool includes a contact trackable element, wherein a tip of the contact trackable element is configured as the detection part, and the tip is configured to move on the current osteotomy plane to provide a point cloud information.

Optionally, in the osteotomy calibration device, the position tracking calibration tool includes an inductive trackable element, wherein an inductive end of the inductive trackable element is configured as the detecting part, and the inductive part is configured to move on the current osteotomy plane to provide a point cloud information.

Optionally, in the osteotomy calibration device, the position tracking calibration tool includes a structured optical scanner, and wherein a scanning part of the structured optical scanner is configured as the detecting part, and the scanning part is configured to scan the current osteotomy plane.

Optionally, in the osteotomy calibration device, the osteotomy calibration device includes a displacement calibration tool, wherein the displacement calibration tool includes two or more sensing surfaces connected in sequence, at least one trackable element and a plurality of displacement sensors, and wherein: the at least one trackable element is connected to the sensing surfaces; the sensing surfaces are connected to the displacement sensors; the displacement sensors are configured to sense displacement information of the current osteotomy plane with respect to a corresponding one of the sensing surfaces; and the sensing surfaces and the displacement sensors are configured as the acquisition unit, and the at least one trackable element is configured as the position tracking unit.

Optionally, in the osteotomy calibration device, a relative position of the position tracking unit with respect to the acquisition unit is fixed.

To solve the above technical problems, according to a third aspect of the invention, there is provided an orthopedic surgery system, comprising:

a control device, a navigation device, a robotic arm, and an osteotomy calibration device, wherein the osteotomy calibration device comprises an acquisition unit and a position tracking unit, wherein: the acquisition unit is configured to acquire a position information of a current osteotomy plane; the position tracking unit is connected to the acquisition unit, and the position tracking unit is configured for position tracking by a navigation device; each of the position information of the current osteotomy plane acquired by the acquisition unit and a position information of the position tracking unit in the navigation device is used to determine a calculated position information of the current osteotomy plane;

wherein the navigation device matches with the position tracking unit of the osteotomy calibration device so as to obtain a position information of the position tracking unit and feedback the position information to the control device; and wherein the control device is configured to obtain the calculated position information of a current osteotomy plane according to the position information of the position tracking unit of the osteotomy calibration device, and to determine a position error between the calculated position information and a predetermined position information of a planned osteotomy plane, and if the position error exceeds a preset value, the control device drives and relocates the robotic arm Optionally, in the orthopedic surgery system, further comprising: a position tracking calibration tool including a detection part and a trackable element connected to the detection part, the detection part is configured as the acquisition unit, and the trackable element is configured as the position tracking unit.

Optionally, in the orthopedic surgery system, the position tracking calibration tool includes a contact trackable element, wherein a tip of the contact trackable element is configured as the detection part, and the tip is configured to move on the current osteotomy plane to provide a point cloud information.

Optionally, in the orthopedic surgery system, the position tracking calibration tool includes an inductive trackable element, wherein an inductive end of the inductive trackable element is configured as the detecting part, and the inductive part is configured to move on the current osteotomy plane to provide a point cloud information.

Optionally, in the orthopedic surgery system, the position tracking calibration tool includes a structured optical scanner, and wherein a scanning part of the structured optical scanner is configured as the detecting part, and the scanning part is configured to scan the current osteotomy plane.

Optionally, in the orthopedic surgery system, comprising a displacement calibration tool, wherein the displacement calibration tool includes two or more sensing surfaces connected in sequence, at least one trackable element and a plurality of displacement sensors, and wherein: the at least one trackable element is connected to the sensing surfaces; the sensing surfaces are connected to the displacement sensors; the displacement sensors are configured to sense displacement information of the current osteotomy plane with respect to a corresponding one of the sensing surfaces; and the sensing surfaces and the displacement sensors are configured as the acquisition unit, and the at least one trackable element is configured as the position tracking unit.

In summary, in an osteotomy calibration method, calibration tool, a readable storage medium, and an orthopedic surgery system provided by the present application, firstly using the osteotomy calibration device to obtain the calculated position information of the current osteotomy plane, and then determining a position error between the calculated position information and a predetermined position information of a planned osteotomy plane, and if the position error exceeds a preset value, calculating and transmitting a relocation information to a robotic arm so as to control and relocate the robotic arm. In this way, by comparing and identifying the position error between the current osteotomy plane formed by the first osteotomy and the planned predetermined osteotomy plane, relocating the robotic arm and performing a secondary correction for the osteotomy plane, which can improve the final accuracy of the osteotomy plane. In addition, by relocating the robotic arm and performing the secondary correction for the osteotomy plane, additional bone nails which is to fix the navigation tool to the bone can be avoided. Therefore, the patient's trauma surface and surgical time can be reduced.

BRIEF DESCRIPTION OF THE DRAWINGS

Those of ordinary skill in the art will understand that the accompanying drawings are provided for better understanding of the present application, and do not limit the scope of the present application in any way, in which.

In these drawings.

Figure 1:
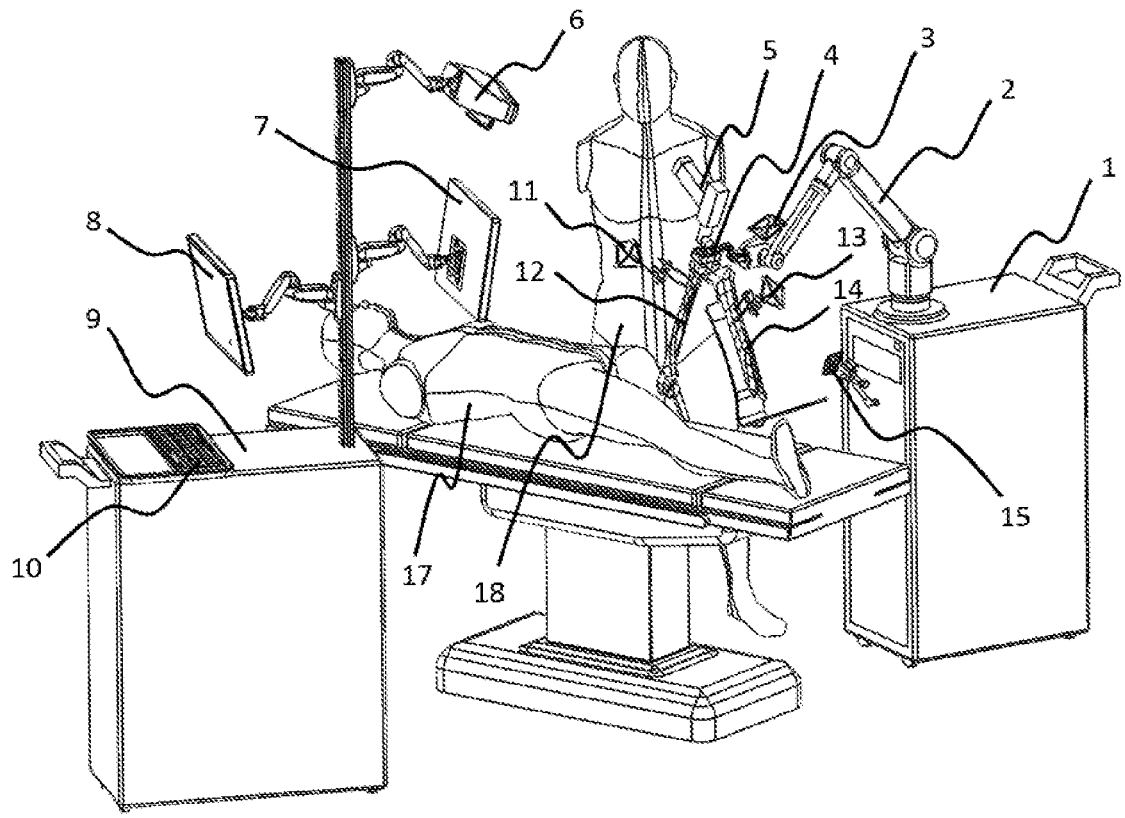
FIG. 1 is a schematic diagram of knee arthroplasty by using orthopedic surgery system according to Embodiment 1 of the present application.

1: a surgical trolley; 2: a robotic arm; 3: a tool trackable element; 4: an osteotomy navigation tool; 5: a pendulum saw; 6: an NDI navigation device; 7: an auxiliary display; 8: a main display; 9: a navigation trolley; 10: a keyboard; 11: a femoral trackable element; 12: a femur; 13: a tibia trackable element; 14: a tibia; 15: a base trackable element; 17: a patient; 18: an operator; 121: a tip; 122: an inductive part; 123: a scanning part; 131: a sensing surface; 132: a displacement sensor; 200: a trackable element.

DETAILED DESCRIPTION

Features and advantages of the invention will be more apparent from the following detailed description. It is noted that the figures are provided in a very simplified form and not necessarily drawn to scale, with the only intention to facilitate convenience and clarity in explaining the embodiment. In addition, the structures shown in the drawings are often a part of the actual structure. In particular, different emphasis of the drawings is needed to be shown, and sometimes different scales are used.

As used in the present application, the singular forms "a," "an," and "the" include plural referents unless otherwise specified in the content. As used in the present application, the term "or" is generally used in a meaning including "and/or" unless otherwise specified in the content. As used in the present application, the term "multiple" is generally used in a meaning including "at least one" unless otherwise specified in the content. As used in the present application, the term "at least two" is generally used in a meaning including "two or more" unless otherwise specified in the content. In addition, the terms "first", "second", and "third" are used for descriptive purposes only, and cannot be understood as indicating or implying relative importance or implicitly indicating the number of technical features indicated. Therefore, the features defined as "first", "second", and "third" may explicitly or implicitly include one or at least two of the features.

The core idea of the present application is to provide to an osteotomy calibration method, a calibration device, a readable storage medium, and an orthopedic surgery system to solve the problem of low accuracy of the existing osteotomy.

The osteotomy calibration method comprises: obtaining a calculated position information of a current osteotomy plane using an osteotomy calibration device; determining a position error between the calculated position information and a predetermined position information based on a planned osteotomy plane, and if the position error exceeds a preset value, calculating and transmitting a relocation information to a robotic arm so as to control and relocate the robotic arm.

The osteotomy calibration device includes the acquisition unit and the position tracking unit. The acquisition unit is configured to acquire a position information of a current osteotomy plane and the position tracking unit is connected to the acquisition unit and has a fixed relative position therebetween, and the position tracking unit is configured for position tracking by a navigation device. Each of the position information of the current osteotomy plane acquired by the acquisition unit and a position information of the position tracking unit in the navigation device is used to determine a calculated position information of the current osteotomy plane.

The readable storage medium has a program stored thereon, and when the program is executed, the program is implemented according to the osteotomy calibration method as described above.

The orthopedic surgery system comprises a control device, a navigation device, a robotic arm, and an osteotomy calibration device described above, wherein the osteotomy calibration device comprises an acquisition unit and a position tracking unit, wherein: the acquisition unit is configured to acquire a position information of a current osteotomy plane; the position tracking unit is connected to the acquisition unit, and the position tracking unit is configured for position tracking by a navigation device; each of the position information of the current osteotomy plane acquired by the acquisition unit and a position information of the position tracking unit in the navigation device is used to determine a calculated position information of the current osteotomy plane; wherein the navigation device matches with the position tracking unit of the osteotomy calibration device so as to obtain a position information of the position tracking unit and feedback the position information to the control device; and wherein the control device is configured to obtain the calculated position information of a current osteotomy plane according to the position information of the position tracking unit of the osteotomy calibration device, and to determine a position error between the calculated position information and a predetermined position information of a planned osteotomy plane, and if the position error exceeds a preset value, the control device drives and relocates the robotic arm.

In this way, by comparing and identifying the position error between the current osteotomy plane formed by the first osteotomy and the planned predetermined osteotomy plane, the robotic arm is relocated, and then the osteotomy plane is performed by a further or secondary correction, which can improve the final accuracy of the osteotomy plane. In addition, by relocating the robotic arm and performing the secondary correction of the osteotomy plane, additional bone nail which is used to fix the navigation tool to the bone can be avoided. Therefore, the patient's trauma surface and surgical time can be reduced.

The following description is made with reference to the drawings.

Embodiment 1

Figure 2:
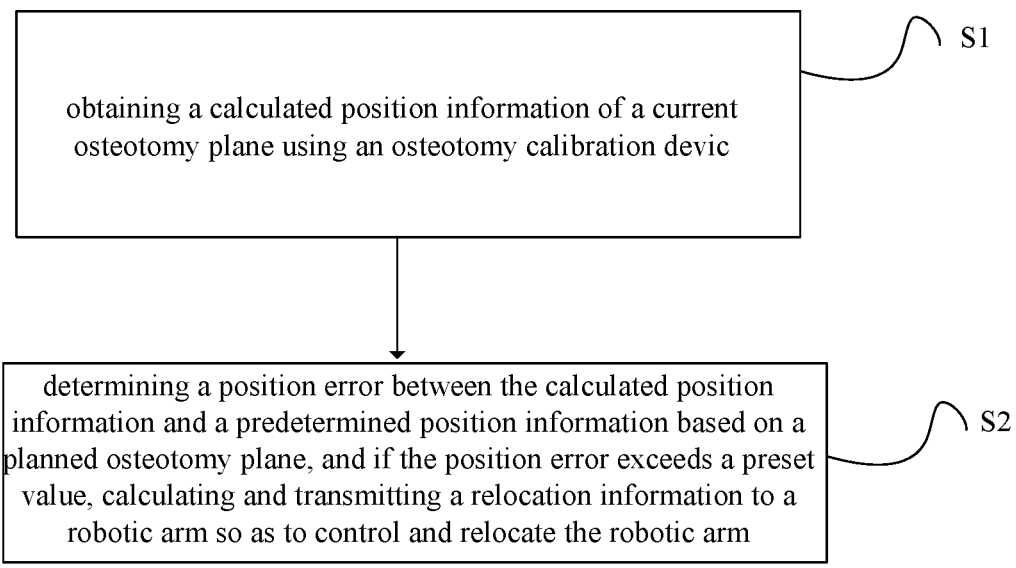
FIG. 2 is a flowchart of an osteotomy calibration method according to Embodiment 1 of the present application.
Figure 3:
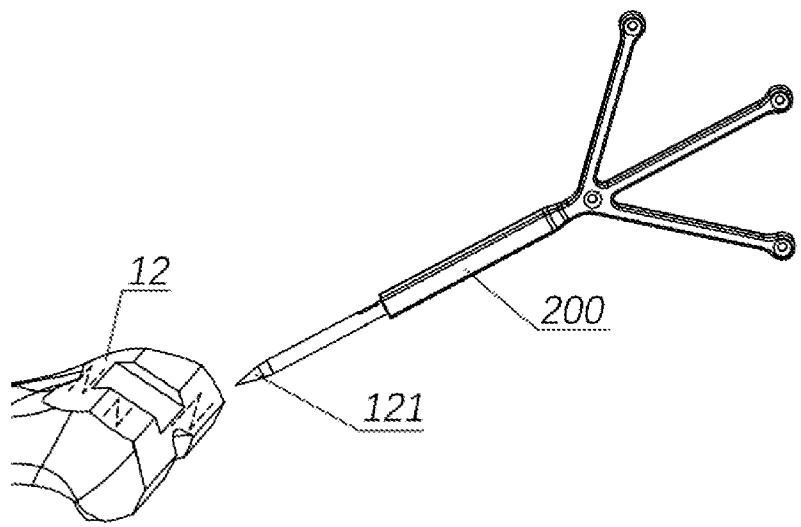
FIG. 3 is a schematic diagram of usage of an osteotomy calibration device according to a first example of Embodiment 1 of the present application.
Figure 4:
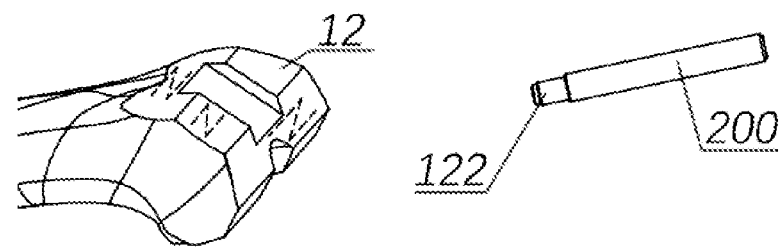
FIG. 4 is a schematic diagram of an osteotomy calibration device according to a second example of Embodiment 1 of the present application.
Figure 5:
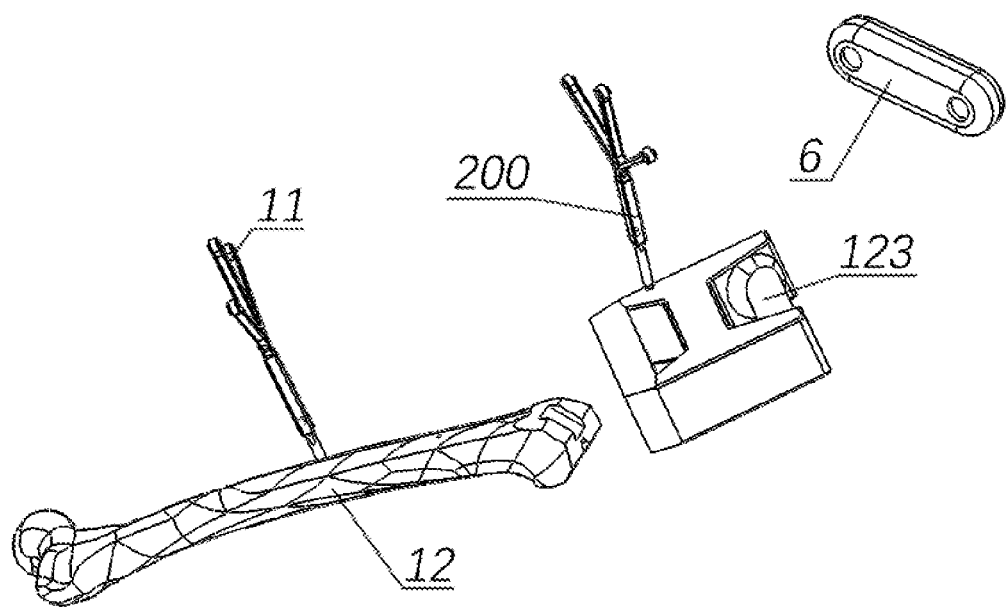
FIG. 5 is a schematic diagram of an osteotomy calibration device according to a third example of Embodiment 1 of the present application.

Referring to FIGS. 1 to 5, FIG. 1 is a schematic diagram of knee arthroplasty by using orthopedic surgery system according to Embodiment 1 of the present application; FIG. 2 is a flowchart of an osteotomy calibration method according to Embodiment 1 of the present application; FIG. 3 is a schematic diagram of usage of an osteotomy calibration device according to a first example of Embodiment 1 of the present application; FIG. 4 is a schematic diagram of an osteotomy calibration device according to a second example of Embodiment 1 of the present application; FIG. 5 is a schematic diagram of an osteotomy calibration device according to a third example of Embodiment 1 of the present application.

Embodiment 1 of the present application provides an orthopaedic surgical system. FIG. 1 shows a schematic diagram of knee arthroplasty by using the orthopaedic surgical system. However, the orthopaedic surgical system of the present application has no particular limitation on the application environment and can also be applied to other orthopedic surgery. In the following description, an orthopaedic surgical system is described by using knee joint arthroplasty as an example, but it should not be used to limit the present application.

As shown in FIG. 1, the orthopedic surgery system includes a control device, a navigation device, a robotic arm 2, and an osteotomy navigation tool 4. In some embodiments, the control device is a computer. The computer is equipped with a controller, a main display 8 and a keyboard 10, and more preferably also includes an auxiliary display 7. In Embodiment 1, the contents displayed on the auxiliary display 7 and the main display 8 are the same, for example, both are used to display an osteotomy position image. The navigation device is selected as an electromagnetic positioning navigation device, an optical positioning navigation device, or an electromagnetic positioning navigation device. Preferably, the navigation device is an optical positioning navigation device. Compared with other navigation methods, the optical positioning navigation has a high measurement accuracy, which can effectively improve the positioning accuracy of the osteotomy navigation tool. In the following description, the optical positioning and navigation device is taken as an example for description, but is not limited thereto.

The navigation device includes a navigation marker and a tracker 6. The navigation marker includes a base trackable element 15 and a tool trackable element 3. The base trackable element 15 is fixed, for example, the base trackable element 15 is fixed on the surgical trolley 1 to provide a base coordinate system (also referred to as a base trackable element coordinate system). The tool trackable element 3 is mounted on the osteotomy navigation tool 4 to track the position of the osteotomy navigation tool 4. The osteotomy navigation tool 4 is installed at the end of the robotic arm 2 so that the osteotomy navigation tool 4 is supported by the robotic arm 2 and the spatial position and pose of the osteotomy navigation tool 4 are adjusted.

In practice, the tracker 6 is used to capture the signal (such as an optical signal) reflected by the tool trackable element 3 and record the position of the tool trackable element 3 (that is, the position and pose of the tool trackable element under the base trackable element system). The computer program stored in the memory of the control device controls the movement of the robotic arm 2 according to the current position and the desired position of the tool trackable element. The robotic arm 2 drives the osteotomy navigation tool 4 and the tool trackable element 3 to move so that the tool trackable element 3 reaches the desired position. The desired position of the tool trackable element 3 corresponds to the desired position of the osteotomy navigation tool 4.

Therefore, for the application of the orthopaedic surgery system, the automatic positioning of the osteotomy navigation tool 4 can be realized, and the real-time pose of the osteotomy navigation tool 4 is tracked and fed back by the tool trackable element 3 during the operation, and the adjustment of the position and pose of the osteotomy navigation tool 4 is achieved by controlling the movement of the robotic arm. The osteotomy navigation tool 4 not only achieves a high positioning accuracy, but also is supported by the robotic arm 2, that is, no need to fix the navigation tool to the human body, which can avoid the secondary or a further injury to the human body.

Generally, the orthopedic surgery system further includes a surgical trolley 1 and a navigation trolley 9. The control device and a part of the navigation device are installed on the navigation cart 9, for example, the controller is installed inside the navigation cart 9, and the keyboard 10 is placed outside the navigation trolley 9 for operation. Each of the main display 8, the auxiliary display 7 and the tracker 6 is mounted on a bracket, the bracket is vertically fixed on the navigation trolley 9, and the robotic arm 2 is mounted on the surgical trolley 1. The use of the surgical trolley 1 and the navigation trolley 9 makes the entire surgical operation more convenient.

When performing knee arthroplasty surgery, the use of the orthopedic surgery system of Embodiment 1 generally includes the following operations:

firstly, moving the surgical trolley 1 and the navigation trolley 9 to appropriate positions next to the hospital bed;

secondly, installing navigation markers (the navigation markers also include the femoral trackable element 11 and the tibial trackable element 13), the osteotomy navigation tool 4, and other related components (such as sterile bags);

thirdly, the operator 18 imports the CT/MR scan model of the bone of the patient 17 into the computer for preoperative planning so as to obtain an osteotomy plan which includes, for example, the coordinates of the osteotomy plane, the model of the prosthesis, and the installation orientation of the prosthesis and other information; particularly, based on the patient's knee joint image data obtained from the CT/MR scan, a three-dimensional digital model of the knee joint is created, and then an osteotomy plan is created based on the three-dimensional digital model of the knee joint, so that the operator can perform preoperative evaluation according to the osteotomy plane. More specifically, the osteotomy plan is determined based on the three-dimensional digital model of the knee joint, and the obtained prosthesis size specifications and the installation position of the osteotomy plate. The osteotomy plan is finally output in the form of a surgical report, which records a series of reference data such as osteotomy plane coordinates, osteotomy amount, osteotomy angle, prosthesis specifications, installation position of prosthesis, surgical aids, etc, especially includes a series of theoretical explanations, such as the reason for selection of the osteotomy angle and etc, so as to provide a reference for surgical operators. Among them, the three-dimensional digital model of the knee joint can be displayed on the main display 8 and the operator can input surgical parameters by keyboard 10 to facilitate preoperative planning;

after the preoperative evaluation, the operator 18 then uses the trackable element pen to mark feature points on the patient's femur and tibia (that is, the operator marks multiple femoral anatomical feature points on the patient's femoral, and multiple tibial anatomical features on the tibia), and the navigation device (taking the base trackable element 15 as a reference) is configured to record the positions of all feature points on the patient's tibia 14 and femur 12, and send the positions of all feature points to the controller, and then the controller obtains the actual orientation of the femur 12 and the tibia 14 by matching algorithm. The actual orientation of the femur 12 and the tibia 14 corresponds to the CT/MR image orientation of the femur 12 and the tibia 14;

subsequently, the actual orientation of the femur and tibia is linked to the corresponding trackable element mounted on the femur and tibia through the navigation device, so that the femoral trackable element 11 and the tibia trackable element 13 can track the actual position of the bone in real time. During the surgery, as long as the relative position of the trackable element with respect to the bone is fixed, the bone movement will not affect the surgical effect;

further, the coordinate of the osteotomy plane planned before the operation is sent to the robotic arm 2 through the navigation device. After the robotic arm 2 locates the osteotomy plane through the tool trackable element 3 and moves to the predetermined position, the robotic arm 2 keeps in the holding state (that is, does not move)). After that, the operator can perform osteotomy and/or drilling operations with the osteotomy navigation tool 4 by using a surgical tool 5 such as a pendulum saw or an electric drill. After the osteotomy and drilling operations have been completed, the operator can install the prosthesis and perform other surgical operations.

Traditional surgery and navigation surgery systems without robotic arm for positioning require manual adjustment of the osteotomy navigation positioning tool, which has a poor accuracy and a low adjustment efficiency. With the use of a robotic arm positioning navigation tool, the operator does not need to fix the navigation tool on the bones by additional bone nails, so that the patient's trauma surface and the operation time are reduced.

In Embodiment 1, the navigation marker further includes a femur trackable element 11 and a tibial trackable element 13. The femoral trackable element 11 is used to locate the spatial position and pose of the femur 12, and the tibial trackable element 13 is used to locate the spatial position and pose of the tibia 14. As mentioned before, the tool trackable element 3 is mounted on the osteotomy navigation tool 4, but in other embodiments, the tool trackable element 3 may also be mounted on the end joint of the robotic arm 2.

Based on the above orthopedic surgery system, robot-assisted surgery can be achieved, which helps the operator to locate the osteotomy position so that to facilitate the osteotomy operation. After the operator performs the osteotomy by an orthopaedic surgical system or other methods (such as performing the osteotomy manually without robotic assistance), multiple osteotomy planes can be obtained, hereinafter referred to as the current osteotomy plane. As described in the Background, accuracy of the current osteotomy plane is limited due to reasons such as positioning accuracy of the robotic arm and saw blade swing. Therefore, Embodiment 1 provides an osteotomy calibration method, including:

step S1: obtaining a calculated position information of a current osteotomy plane using an osteotomy calibration device;

step S2: determining a position error between the calculated position information and a predetermined position information based on a planned osteotomy plane, and if the position error exceeds a preset value, calculating and transmitting a relocation information to a robotic arm 2 so as to control and relocate the robotic arm.

By comparing and identifying the position error between the current osteotomy plane formed by the first osteotomy and the planned predetermined osteotomy plane, relocating the robotic arm 2, and performing a secondary correction for the osteotomy plane, which can improve the final accuracy of the osteotomy plane. In addition, by relocating the robotic arm 2 and performing the secondary correction for the osteotomy plane, additional bone nails which is to fix the navigation tool to the bone can be avoided. Therefore, the patient's trauma surface and surgical time can be reduced.

To achieve the above osteotomy calibration method, Embodiment 1 provides an osteotomy calibration device including an acquisition unit and a position tracking unit. The acquisition unit is configured to acquire a position information of a current osteotomy plane; and the position tracking unit is configured for position tracking by a navigation device; each of the position information of the current osteotomy plane is acquired by the acquisition unit, and a control device uses a position information of the position tracking unit in the navigation device to calculate a calculated position information of the current osteotomy plane. In some embodiments, the position tracking unit is connected to the acquisition unit and has a fixed relative position with respect thereto, so as to facilitate a coordinate transformation for the position information of the acquisition unit by the control device.

In Embodiment 1, the osteotomy calibration device includes a position tracking calibration tool. The position tracking calibration tool includes a detection part and a trackable element 200 connected to the detection part, the detection part is configured as the acquisition unit, and the trackable element 200 is configured as the position tracking unit. In some embodiments, the trackable element 200 includes four reflective spheres 201, and the four reflective spheres 201 form a geometric array which is recognized by the optical navigation system NDI (namely one of the aforementioned navigation device). The relative position of the detection part with respect to the trackable element 200 is fixed, and the relative positional relationship is stored in a storage device in advance. Specifically, the optical navigation system is configured to receive/track the information fed back by the reflective sphere 201 on the trackable element 200, thus the position information of the trackable element 200 is obtained, and then the position information is sent to the control device. The control device according to the prestored positional relationship of the trackable element with respect to the detection part, calculating a position information of a detection part, and obtaining a calculated position information of a current osteotomy plane by a position information detected by the detection part; determining a position error between the calculated position information and a predetermined position information based on a predetermined position information (prestored in a storage device) of a planned osteotomy plane, and if the position error exceeds a preset value, calculating and transmitting a relocation information to a robotic arm 2 so as to control and relocate the robotic arm 2. Apparently, the relative positional relationship between the detection part and the trackable element referred to here is fixed, and it is not limited that those two must be fixedly connected, rather the relative positional relationship therebetween after assembly is fixed. In some embodiments, the detection part and the trackable element are detachably connected.

When the osteotomy calibration device is deformed or the detection part needs to be replaced, the detection part can be directly replaced without replacing the entire osteotomy calibration device. Further, the orthopedic surgery system includes the osteotomy calibration device as described above. The navigation device 6 matches with the position tracking unit of the osteotomy calibration device so as to obtain a position information of the position tracking unit and feedback the position information to the control device; the control device is configured to obtain a calculated position information of a current osteotomy plane according to the position information of the position tracking unit of the osteotomy calibration device, and to determine a position error between the calculated position information and a predetermined position information of a planned osteotomy plane, and if the position error exceeds a preset value, the control device drives and relocates the robotic arm 2. Specifically, the position error is superimposed on the predetermined position information to obtain relocation information, and the relocation information is transmitted to the robotic arm 2 so as to relocate the robotic arm.

Further, the step S1 includes: obtaining a point cloud information according to a movement (such as Z-shaped or S-shaped sliding or multi-point click movement) of the position tracking calibration tool on the current osteotomy plane, or according to a scan of the current osteotomy plane by the position tracking calibration tool; collecting the point cloud information obtained by the position tracking calibration tool, and fitting the point cloud information to a fitting plane; and calculating a position information of the fitting plane, and defining the position information of the fitting plane as the calculated position information of the current osteotomy plane.

Optionally, the calculated position information includes a calculating normal vector and a calculated position, and the step of calculating the position information of the fitting plane includes: determining a calculating normal vector $\vec{n}_V$ and a calculated position $P_V(x_V,y_V,z_V)$ of the fitting plane in a lower limb DICOM (Digital Imaging and Communications in Medicine) data coordinate system based on a normal vector $\vec{n}_P$ and a position $P_P(x_P,y_P,z_P)$ of the fitting plane in a trackable element coordinate system (that is the reflective spherical coordinate system) of the position tracking calibration tool, and a transformation matrix $M_{P \to V}$ between the trackable element coordinate system and the lower limb DICOM data coordinate system. Optionally, when coordinate transformation is performed between the trackable element coordinate system and the lower limb DICOM data coordinate system, femoral (or tibia) trackable element coordinate system is indirectly used due to the trackable element on the femur (or tibia) and the trackable element 200 of position tracking calibration tool in the optical navigation system NDI has their own position and pose information. Specifically, firstly through the transformation matrix $M_{P \to V}$ between the trackable element coordinate system and the femur (or tibia) trackable element coordinate system, the normal vector $\vec{n}_P$ and the position $P_P(x_P,y_P,z_P)$ of the fitting plane in the trackable element coordinate system are transferred into a normal vector $\vec{n}_B$ and a position $P_B(x_B,y_B,z_B)$ in the femur (or tibia) trackable element coordinate system, then the normal vector $\vec{n}_B$ and the position $P_B(x_B,y_B,z_B)$ of the fitting plane in femur (or tibia) trackable element coordinate system are transferred into the calculating normal Vector $\vec{n}_V$ and the calculated position $P_V(x_V,y_V,z_V)$ in the lower limb DICOM data coordinate system through a transformation matrix $M_{B \to V}$ between femur (or tibia) reflective spherical coordinate system and the lower limb DICOM data coordinate.

Further, the position error includes: calculating a normal vector rotation matrix of the calculating normal vector and a predetermined normal vector based on the predetermined normal vector and the predetermined position of the planned osteotomy plane; and calculating a position deviation between the calculated position and the predetermined position of the planned osteotomy plane. Specifically, the calculating normal vector $\vec{n}_V$ and the calculated position $P_V(x_V,y_V,z_V)$ of the fitting plane in a lower limb DICOM data coordinate system are respectively compared with the predetermined normal vector $\vec{n}_O$ and the predetermined position $P_O(x_O,y_O,z_O)$ of the planned osteotomy plane. Through two normal vectors, an euler angle between the fitting plane and the planned osteotomy plan is obtained, thereby obtaining the rotation matrix $R_{3\times3}$. Rotating the fitting plane to be parallel to the planned osteotomy plane through the rotation matrix $R_{3\times3}$ and a distance $\vec{d}$ between the two planes is calculated. The normal vector rotation matrix $R_{3\times3}$ and the position deviation $\vec{d}$ are the position error between the fitting plane and planned osteotomy plane. Since the fitting plane represents the current osteotomy plane, the normal vector rotation matrix $R_{3\times3}$ and the position deviation $\vec{d}$ are the position error between the current osteotomy plane and the planned osteotomy plane.

Furthermore, after determining the position deviation between the calculated position and the predetermined position, if at least one of the normal vector rotation matrix $R_{3\times3}$ (the amount of rotation of each axis after the normal vector rotation matrix $R_{3\times3}$ transformed into the euler angle) and the position deviation $\vec{d}$ exceeds a preset value, then the normal vector rotation matrix $R_{3\times3}$ and the position deviation $\vec{d}$ are superimposed on the predetermined position information to obtain relocation information, and transmitting the relocation information to a robotic arm so as to control and relocate the robotic arm. Those skilled in the art can set an appropriate preset value to the normal vector rotation matrix $R_{3\times3}$ and the position deviation $\vec{d}$ according to the actual situation, when at least one of the normal vector rotation matrix $R_{3\times3}$ and the position deviation $\vec{d}$ exceeds the preset value, it can be considered that the accuracy of the current osteotomy plane formed by the first osteotomy does not meet the requirements, and a second osteotomy is required. Thus the normal vector rotation matrix $R_{3\times3}$ and the position deviation $\vec{d}$ are transmitted to robotic arm 2 so as to relocate the robotic arm 2, and further relocate the osteotomy. Therefore, a more accurate osteotomy result is obtained. Contrarily, if each of the normal vector rotation matrix $R_{3\times3}$ and the position deviation $\vec{d}$ is in accordance with the preset values, that is, the accuracy of the current osteotomy plane meets the requirements, and the surgical procedure can be continued.

It should be understood that in the above description, four reflective spheres are schematically used as the trackable element 200. The arrangement of the reflective spheres is not limited to a rectangular distribution, it can also be distributed like a tree, and the number of reflective spheres is not limited to four as well. It should be noted that the trackable element 200 is not limited to the form of an optical trackable element sphere. The magnetic coil 202 is used as the trackable element 200. Specifically, a 5DOF coil can be used as the trackable element 200, and the end of the cable of the coil is connected to the SIU module 203. In this configuration, the navigation device can use the NDI magnetic navigation AURORA. In this way, the position information of the trackable element 200 is also obtained by sensing the position and orientation of the coil. It should be understood that the above osteotomy calibration is performed either after each osteotomy step is completed, or performed at one time after multiple osteotomy steps are completed. The timing of osteotomy calibration is determined according to operating habits, that is to say, when to perform the osteotomy calibration is determined according to operating habits.

Referring to FIG. 3, in Embodiment 1, the position tracking calibration tool includes contact trackable element, and a tip 121 of the contact trackable element is configured as the detection part, and the tip is used to slide on the osteotomy plane in a Z shape to obtain the position information (mainly the position information of several feature points of the Z shape) of the current osteotomy plane. Preferably, the tip 121 of the contact trackable element is used to contact the current osteotomy plane, and the trackable element 200 is a reflective sphere trackable element, which is disposed at the other end of the contact trackable element opposite to the tip 121. In this configuration, the navigation device 6 can obtain the position information of the tip 121 through the trackable element 200. When the tip 121 contacts the current osteotomy plane, it can move or slide in different paths on the current osteotomy plane, such as a "Z" shape sliding or an "S" shape sliding, multi-click movement and etc. to collect as much point cloud information as possible. Further, after the tip completes the movement in the current osteotomy plane, the control device can remove the invalid points in the point cloud information, and then fit the effective point cloud information into a virtual fitting plane, and extract geometric position center and normal vector of the fitting plane, and the geometric position center and normal vector are transformed into the calculated position and normal vector in the lower limb DICOM data coordinate system through the transformation relationship between the coordinate systems, that is, the calculated position information of the current osteotomy plane is obtained. It should be understood that the sliding trajectory of the tip is not limited to a "Z" shape, but may also be other shapes, such as a rectangular shape, a shape defined by any lines or points.

In some embodiments, the position tracking calibration tool is used to calibrate two or more current osteotomy planes, and wherein, prior to fitting the point cloud information to the fitting plan, the step of obtaining the calculated position of the current osteotomy plane using the osteotomy calibration device further includes: dividing the point cloud information into respective groups corresponding to the two or more current osteotomy planes through clustering; and for each group of the groups of point cloud information, removing invalid point cloud information from the group, and fitting remaining point cloud information in the group to a corresponding fitting plane. In an exemplary embodiment, after performing the osteotomy, the femur obtains 5 current osteotomy planes, namely: a femoral distal end plane, a femoral distal end beveling plane, a femoral distal end anterior beveling plane, a femoral distal end posterior beveling plane, a femoral distal end posterior cut plane. The control device may divide the point cloud information obtained by the navigation device into 5 groups by clustering, so as to respectively fit the point cloud information to 5 fitting planes and further to obtain position information of the 5 fitting planes. Furthermore, matching the predetermined position information of the 5 planned osteotomy planes with the actual measured position information of the fitting planes (that is, the calculated position information of the current osteotomy plane) by clustering method, and calculating the position errors between the calculated position information of the current osteotomy planes and positions of the corresponding planned osteotomy planes, and if any one of the position errors exceeds a preset value, the osteotomy is relocated, so as to obtain a more accurate osteotomy result.

Referring to FIG. 4, in a second example of Embodiment 1, the position tracking calibration tool includes inductive trackable element. An inductive end 122 of the inductive trackable element is configured as the detecting part, and the inductive part is configured to move on the current osteotomy plane in a Z shape. In some embodiments, the inductive end 122 of the inductive trackable element is configured to sense the current osteotomy plane and to obtain the position information (mainly the position information of several feature points of the Z shape) of the current osteotomy plane. The trackable element 200 is a reflective sphere trackable element, which is disposed at the other end of the contact trackable element opposite to inductive end 122. In an exemplary embodiment, the inductive trackable element is an active infrared inductive trackable element, and the inductive end 122 can emit infrared rays. By sensing the reflected signal, the position information of the aligned points (located on the current osteotomy plane) can be known. In this configuration, the navigation device 6 can obtain the position information of the inductive end 122 through the trackable element 200. When the inductive end 122 is aligned with the current osteotomy plane, it slides in a "Z" shape so as to collect as much point cloud information as possible. After collecting enough point cloud information, the fitting plane can be generated.

Referring to FIG. 5, in a third example of Embodiment 1, the position tracking calibration tool includes a structured optical scanner, and wherein a scanning part 123 of the structured optical scanner is configured as the detecting part, and the scanning part 123 is configured to scan the current osteotomy plane so as to obtain the position information of the current osteotomy plane. In some embodiments, the scanning part 123 of the structured optical scanner is used to scan the current osteotomy plane. The trackable element 200 is a reflective sphere trackable element, which is arranged on the structured optical scanner, and the scanning part 123 of the structured light scanner and the trackable element are aligned before use, so as to obtain information of the scanning part 123 in the local coordinate system of the trackable element 200. The scanning part 123 of the structured optical scanner can obtain the position information of the current osteotomy plane by scanning, and then transmit it to the control device. The control device obtains the calculated position information of the current osteotomy plane through the coordinate transformation relationship between the local coordinate system of the trackable element 200 and the lower limb DICOM data coordinate system.

According to the above method, by comparing and identifying the position error between the current osteotomy plane formed by the first osteotomy and the planned predetermined osteotomy plane, the robotic arm is relocated, and then a secondary correction of the osteotomy plane is performed, such that the final accuracy of the osteotomy plane is improved. Moreover, by relocating the robotic arm 2 and performing the secondary correction of the osteotomy plane, additional bone nails configured to repeatedly fix the navigation tool on the bone can be avoided, such that trauma surface of the patient is reduced, and the operation time is shorten. Apparently, the calibration may be performed immediately after an osteotomy, or the calibration may be performed in sequence after all the osteotomy steps are completed. Based on this, this embodiment also provides a readable storage medium on which a program is stored, and when the program is executed, the osteotomy calibration method as described above is implemented. In addition, the above program can also be integrated into a hardware device, such as integrating the program into the control device of the orthopedic surgery system.

Embodiment 2

Figure 6:
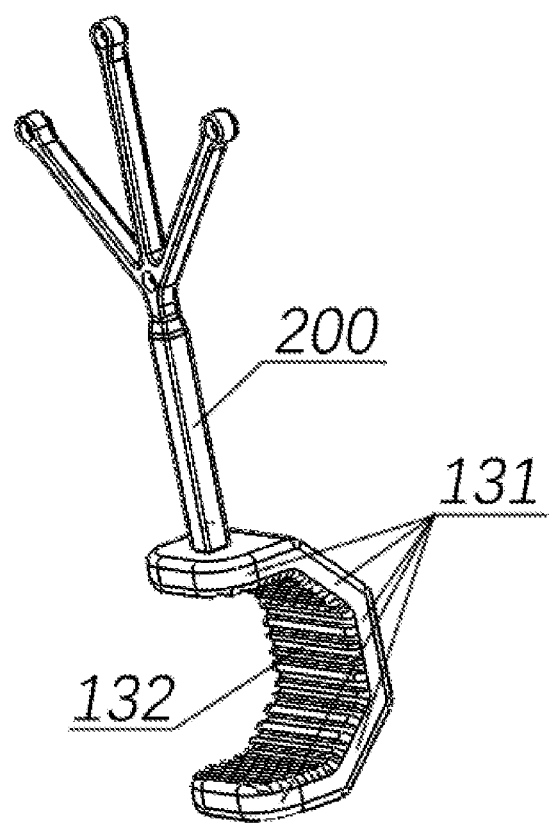
FIG. 6 is a schematic diagram of an osteotomy calibration device according to Embodiment 2 of the present application.

Referring to FIG. 6, which is a schematic diagram of an osteotomy calibration device according to Embodiment 2 of the present application.

The osteotomy calibration method, calibration device, a readable storage medium, and an orthopedic surgery system provided by Embodiment 2 are substantially similar to those provided by Embodiment 1. Basically the same parts will not be described, only the differences will be described below.

In Embodiment 2, the osteotomy calibration device comprises a displacement calibration tool, wherein the displacement calibration tool includes two or more sensing surfaces 131 connected in sequence, at least one trackable element 200 and a plurality of displacement sensors 132, and wherein: the at least one trackable element 200 is connected to the sensing surfaces 131; the sensing surfaces 131 are connected to the displacement sensors 132; the displacement sensors 132 are configured to sense displacement information of the current osteotomy plane with respect to a corresponding one of the sensing surfaces 131; and the sensing surfaces 131 and the displacement sensors 132 are configured as the acquisition unit, and the at least one trackable element 200 is configured as the position tracking unit.

In Embodiment 2, the step of obtaining the calculated position information of the current osteotomy plane using the osteotomy calibration device includes, for each of the two or more current osteotomy planes: acquiring a position information of a corresponding sensing surface 131 of the displacement calibration tool by abutting at least a part of the sensing surface 131 on the current osteotomy plane, the sensing surface provided with a trackable element 200; acquiring a displacement information of the current osteotomy plane with respect to the sensing surface 131; calculating the calculated position information of the current osteotomy plane based on the displacement information of the current osteotomy plane with respect to the sensing surface 131 and a position information of the sensing surface 131 provided with the trackable element.

Referring to FIG. 6, in an exemplary embodiment, the displacement calibration tool includes 5 sensing surfaces 131 connected in sequence, a trackable element 200, and a plurality of displacement sensors 132. The trackable element 200 is connected with the first sensing surface 131, and the sensing surface 131 is connected with the displacement sensor 132. The displacement sensor 132 is installed inside the semi-cylinder formed by the 5 sensing surfaces 131. The shape of the semi-cylinder matches with the general shape of the five current osteotomy planes obtained by osteotomy. When the 5 sensing surfaces 131 of the semi-circular abut the current osteotomy plane, the displacement sensors 132 located on the sensing surfaces 131 generate displacement data, and according to the displacement data, the displacement differences between the current osteotomy planes with respect to the sensing surfaces 131 are calculated. And then based on the displacement differences and the inherent characteristics of the sensing surface 131 (such as the angle between the multiple sensing surfaces 131, etc.), the position information of the current osteotomy plane is calculated. Then according to the position information of the trackable element 200 under the navigation device, the control device can calculate the calculated position information of the current osteotomy plane.

Furthermore, matching the predetermined position information of the 5 planned osteotomy planes with the calculated position information, obtained according to actual measurements, of the corresponding current osteotomy planes by clustering; and calculating the position error between the calculated position information of each of the current osteotomy planes and the predetermined position information of the corresponding one of the planned osteotomy planes, and if any one of the position errors exceeds a preset value, relocation is performed for the osteotomy, such that a more accurate osteotomy result is obtained.

Optionally, the displacement calibration tool further includes a bluetooth transmitter for transmitting data sensed by the displacement calibration tool to the control device so that the calculation is performed by the control device. Of course, those skilled in the art may also transmit data sensed by the displacement calibration tool through other transmission methods.

It should be noted that each exemplary embodiment in the specification is described in a progressive manner. Each focuses on the differences from the others. For the same and similar parts therebetween, please refer to each other. In addition, different parts of the exemplary embodiments can also be used in combination, which is not limited in the present application.

In summary, in an osteotomy calibration method, calibration device, a readable storage medium, and an orthopedic surgery system provided by the present application, firstly using the osteotomy calibration device to obtain the calculated position information of the current osteotomy plane, and then determining a position error between the calculated position information and a predetermined position information of a planned osteotomy plane, and if the position error exceeds a preset value, calculating and transmitting a relocation information to a robotic arm so as to control and relocate the robotic arm. In this way, by identifying and comparing the position error between the current osteotomy plane formed by the first osteotomy and the planned predetermined osteotomy plane, relocating the robotic arm, and performing a secondary correction of the osteotomy plane, which can improve the final accuracy of the osteotomy plane. In addition, by relocating the robotic arm and performing secondary correction of the osteotomy plane, additional bone nails which is to fix the navigation tool to the bone can be avoided. Therefore, the patient's trauma surface and surgical time can be reduced.

The above description is only a description of the embodiments of the present application, and does not limit the scope of the present application. Any changes and modifications made by those skilled in the art in accordance with the above disclosure are within the scope of the claims.

What is claimed is:

1. An osteotomy calibration device, comprising: an acquisition unit and a position tracking unit; wherein:
    the acquisition unit is configured to acquire a position information of a current osteotomy plane;
    the position tracking unit is connected to the acquisition unit, and the position tracking unit is configured for position tracking by a navigation device;
    the position information of the current osteotomy plane acquired by the acquisition unit and a position information of the position tracking unit in the navigation device is used to determine a calculated position information of the current osteotomy plane; and
    the osteotomy calibration device comprises a displacement calibration tool, wherein the displacement calibration tool includes two or more sensing surfaces connected in sequence, at least one trackable element and a plurality of displacement sensors, and wherein: the at least one trackable element is connected to the sensing surfaces; the sensing surfaces are connected to the displacement sensors; the displacement sensors are configured to sense displacement information of the current osteotomy plane with respect to a corresponding one of the sensing surfaces; and the sensing surfaces and the displacement sensors are configured as the acquisition unit, and the at least one trackable element is configured as the position tracking unit.

2. The osteotomy calibration device of claim 1, wherein a relative position of the position tracking unit with respect to the acquisition unit is fixed.

3. An osteotomy calibration method, comprising:
    obtaining a calculated position information of a current osteotomy plane using the osteotomy calibration device of claim 1;
    determining a position error between the calculated position information and a predetermined position information based on a planned osteotomy plane, and if the position error exceeds a preset value, calculating and transmitting a relocation information to a robotic arm so as to control and relocate the robotic arm.

4. The osteotomy calibration method of claim 3, wherein the osteotomy calibration device includes a displacement calibration tool for calibrating two or more current osteotomy planes, and wherein the step of obtaining the calculated position information of the current osteotomy plane using the osteotomy calibration device includes, for each of the two or more current osteotomy planes:
    acquiring a position information of a corresponding sensing surface of the displacement calibration tool by abutting at least a part of the sensing surface on the current osteotomy plane, the sensing surface provided with a trackable element;
    acquiring a displacement information of the current osteotomy plane with respect to the sensing surface;
    calculating the calculated position information of the current osteotomy plane based on the displacement information of the current osteotomy plane with respect to the sensing surface and a position information of the sensing surface provided with the trackable element.

5. The osteotomy calibration method of claim 3, the step of determining the position error between the calculated position information and the predetermined position information includes:
    matching the calculated position information of each of the two or more current osteotomy planes with the predetermined position information of a corresponding planned osteotomy plane by clustering; and calculating the position error between the calculated position information of each of the two or more current osteotomy planes and the predetermined position information of the corresponding planned osteotomy plane.

6. An orthopedic surgery system, comprising a control device, a navigation device, a robotic arm, and an osteotomy calibration device, wherein the osteotomy calibration device comprises an acquisition unit and a position tracking unit, wherein: the acquisition unit is configured to acquire a position information of a current osteotomy plane; the position tracking unit is connected to the acquisition unit, and the position tracking unit is configured for position tracking by a navigation device; each of the position information of the current osteotomy plane acquired by the acquisition unit and a position information of the position tracking unit in the navigation device is used to determine a calculated position information of the current osteotomy plane;
    wherein the navigation device matches with the position tracking unit of the osteotomy calibration device so as to obtain a position information of the position tracking unit and feedback the position information to the control device; and
    wherein the control device is configured to obtain the calculated position information of a current osteotomy plane according to the position information of the position tracking unit of the osteotomy calibration device, and to determine a position error between the calculated position information and a predetermined position information of a planned osteotomy plane, and if the position error exceeds a preset value, the control device drives and relocates the robotic arm.

7. The orthopedic surgery system of claim 6, comprising: a position tracking calibration tool including a detection part and a trackable element connected to the detection part, the detection part is configured as the acquisition unit, and the trackable element is configured as the position tracking unit.

8. The osteotomy calibration device of claim 7, wherein the position tracking calibration tool includes a structured optical scanner, and wherein a scanning part of the structured optical scanner is configured as the detecting part, and the scanning part is configured to scan the current osteotomy plane.

9. The osteotomy calibration device of claim 7, wherein the position tracking calibration tool includes a contact trackable element, wherein a tip of the contact trackable element is configured as the detection part, and the tip is configured to move on the current osteotomy plane to provide a point cloud information.

10. The osteotomy calibration device of claim 7, wherein the position tracking calibration tool includes an inductive trackable element, wherein an inductive end of the inductive trackable element is configured as the detecting part, and the inductive part is configured to move on the current osteotomy plane to provide a point cloud information.

11. The osteotomy calibration device of claim 6, comprising a displacement calibration tool, wherein the displacement calibration tool includes two or more sensing surfaces connected in sequence, at least one trackable element and a plurality of displacement sensors, and wherein: the at least one trackable element is connected to the sensing surfaces; the sensing surfaces are connected to the displacement sensors; the displacement sensors are configured to sense displacement information of the current osteotomy plane with respect to a corresponding one of the sensing surfaces; and the sensing surfaces and the displacement sensors are configured as the acquisition unit, and the at least one trackable element is configured as the position tracking unit.

* * * * *